United States Patent [19]
Lorant

[11] Patent Number: 5,908,618
[45] Date of Patent: Jun. 1, 1999

[54] TOPICAL COMPOSITION CONTAINING AT LEAST ONE PROTEIN

[75] Inventor: Raluca Lorant, Thiais, France

[73] Assignee: L'Oreal, France

[21] Appl. No.: 08/998,651

[22] Filed: Dec. 29, 1997

[30] Foreign Application Priority Data

Dec. 27, 1996 [FR] France .................................... 96 16132

[51] Int. Cl.⁶ .................................................. A61K 7/08
[52] U.S. Cl. ...................... 424/70.5; 424/401; 424/70.1; 424/70.7; 424/70.8; 424/59; 424/74
[58] Field of Search ........................... 424/401, 74, 70.1, 424/59, 70.7, 70.5, 70.8; 514/844, 845, 846, 944

[56] References Cited

U.S. PATENT DOCUMENTS

| | | | |
|---|---|---|---|
| 5,368,850 | 11/1994 | Cauwet et al. . | |
| 5,385,729 | 1/1995 | Prencipe et al. | 424/70.11 |
| 5,449,519 | 9/1995 | Wolf et al. | 424/401 |
| 5,470,551 | 11/1995 | Dubief et al. | 424/70.12 |
| 5,531,993 | 7/1996 | Griat | 424/401 |

FOREIGN PATENT DOCUMENTS 2 698 004   5/1994   France .

OTHER PUBLICATIONS

Derwent Abstract No. 83–714752 for JP 58–99407, Jun. 13, 1983.

*Primary Examiner*—Thurman K. Page
*Assistant Examiner*—Lakshmi Channavajjala
*Attorney, Agent, or Firm*—Finnegan, Henderson, Farabow, Garrett & Dunner, L.L.P.

[57] ABSTRACT

The invention relates to a cosmetic and/or dermatological composition containing at least one protein selected from proteins of plant origin and animal origin, wherein the protein may or may not be hydrolysed, and at least one crosslinked poly(2-acrylamido-2-methylpropanesulphonic acid) polymer neutralized to at least 90%, and to its uses. The composition comprises, distributed randomly, a) from 90 to 99.9% by weight of units of formula (1):

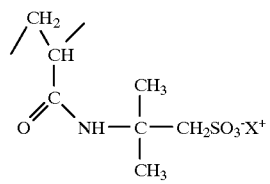

(1)

in which $X^+$ denotes a cation or a mixture of cations, it being possible for at most 10 mol % of the cations $X^+$ to be protons $H^+$; and b) from 0.01 to 10% by weight of crosslinking units resulting from at least one monomer having at least two olefinic double bonds, the proportions by weight being defined with respect to the total weight of the polymer.

30 Claims, No Drawings

TOPICAL COMPOSITION CONTAINING AT LEAST ONE PROTEIN

The invention relates to a cosmetic and/or dermatological composition containing at least one protein of plant origin and/or one protein of animal origin and at least one crosslinked poly(2-acrylamido-2-methylpropanesulphonic acid) polymer neutralized to at least 90% and to its uses.

Cosmetic or dermatological compositions generally exhibit a high viscosity and are mostly formulated in a thickened liquid form, such as a milk, a cream, a gel or a paste. This type of presentation is much appreciated by the consumer; it is more often than not a practical worry for the formulator: facilitating uptake of the product outside its packaging without significant loss, restricting the spreading of the product to the local treatment region and being able to use it in amounts which are sufficient to produce the desired cosmetic or dermatological effect.

This objective is important for formulations such as those of care, hygiene or make-up products which must spread well and homogeneously over the local area to be treated. To satisfy these conditions, the viscosity of the compositions is increased by the addition of thickening and/or gelling polymers. In recent years, protein macromolecules, such as proteins from cereal or oleaginous plant seeds, and animal proteins, such as milk proteins, have been much sought after in cosmetics for their moisturizing properties and their good tolerance with respect to the human body and skin.

The introduction of plant proteins into cosmetic formulations very often leads to destabilization of the latter which is usually reflected by a large fall in viscosity which becomes more significant as the level of protein increases. Moreover, at high concentrations, they contribute a sticky feel of little cosmetic value. In the case of emulsions, instability phenomena can also take the form of creaming, coalescence or phase separation phenomena. This instability could be due to Ostwald ripening. In order to stabilize cosmetic formulations, it is necessary to use thickening agents.

Lipophilic thickening and/or gelling agents, such as fatty acids or alcohols, are generally effective but have a tendency to contribute a greasy and slimy cosmetic feel.

It is preferable to use hydrophilic thickening and/or gelling agents which generally contribute freshness. Unfortunately, many hydrophilic thickening and/or gelling agents behave poorly, or are indeed incompatible, with plant proteins, the presence of which results in a significant loss in their thickening power, which loss increases as the level of protein increases. Moreover, the increase in the concentration of thickening polymer, for the purpose of stabilizing the formulation based on plant protein, usually results in undesirable effects as regards cosmetics, such as a sticky and slimy effect or an unattractive appearance.

For example, natural gums, such as xanthan gum or carrageenans, in the presence of plant proteins have a tendency to render the compositions fluid and stringy. Aqueous gels based on cellulose derivatives lose some of their viscosity in the presence of plant proteins. Certain gelling agents, such as crosslinked polyacrylics of the Carbopol type, are incompatible and, in the presence of plant proteins, result in granular, heterogeneous and unstable aqueous gels.

Mixtures of hydrophilic gelling agents, such as those based on gellan gum and on hydroxyethylcellulose, are incompatible and, in the presence of plant proteins, also result in granular, heterogeneous and unstable aqueous gels.

Certain animal proteins also pose problems of incompatibility with certain thickening or gelling agents. This is the case with serum proteins, such as those resulting from horse serum, in the presence of gelling agents, such as crosslinked polyacrylics of the Carbopol type; the aqueous gels containing them break down and become granular.

One of the objects of the present invention is to be able to produce a great variety of cosmetic or dermatological formulations based on proteins which are stable within a wide range of viscosities and which exhibit good cosmetic properties with respect to appearance, uptake of the product and feel on application.

Moreover, plant or animal proteins are, for the most part, difficult to use in oil-in-water or water-in-oil emulsions. They have a tendency to fluidize the emulsions and to render them unstable. One of the solutions to this problem would be to increase the level of emulsifying surfactants in order to stabilize the oil/water interface but this presents problems because the surfactants generally exhibit an irritation potential with respect to the skin, in particular for sensitive skin.

Another object of the present invention is thus to produce stable and homogeneous oil-in-water or water-in-oil emulsions which can contain high levels of proteins and which exhibit good cosmetic properties with respect to appearance, uptake of the product and feel on application.

The inventor has discovered, surprisingly, a new family of thickening and/or gelling polymers making it possible to obtain stable, thickened cosmetic and dermatological formulations based on proteins of plant or animal origin which contribute good cosmetic properties, such as a soft, non-sticky and smooth feel.

In fact, these specific polymers make it possible to produce homogeneous cosmetic and/or dermatological products which can achieve high viscosities which are stable over time at room temperature or at higher temperatures. They make it possible, in particular, to produce gels or serums which are rich in proteins and which exhibit good stability. Finally, they make it possible to produce, surprisingly, stable and homogeneous oil-in-water or water-in-oil emulsions which can contain proteins in large amounts without contributing a sticky effect to the feel.

The presence of oil in the protein-based emulsions of the invention, thickened and stabilized by the specific polymers defined above, makes it possible to reduce the sticky effects contributed by the proteins used at high concentration levels and to obtain cosmetic products which are light and pleasant in use. Finally, the thickening agents of the invention make it possible to obtain stable protein-rich oil-in-water emulsions without it being necessary to use an emulsifying surfactant.

A subject of the invention is consequently a cosmetic and/or dermatological composition containing, in a cosmetically acceptable medium, at least one protein of plant origin and/or one protein of animal origin, which may or may not be hydrolysed, and at least one crosslinked poly(2-acrylamido-2-methyl-propanesulphonic acid) neutralized to at least 90%.

The crosslinked and virtually or completely neutralized poly(2-acrylamido-2-methylpropanesulphonic acid) polymers in accordance with the invention are water-soluble or swellable in water. They are in general characterized in that they comprise, distributed randomly:

a) from 90 to 99.9% by weight of units of following formula (1):

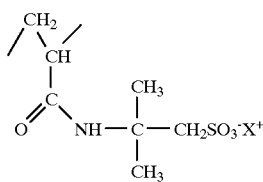
(1)

in which X⁺ denotes a cation or a mixture of cations, it being possible for at most 10 mol % of the cations X⁺ to be protons H⁺;

b) from 0.01 to 10% by weight of crosslinking units resulting from at least one monomer having at least two olefinic double bonds, the proportions by weight being defined with respect to the total weight of the polymer.

The polymers of the invention preferentially contain a number of units of formula (1) in an amount which is sufficiently high to produce a hydrodynamic volume of the polymer in solution in water having a radius ranging from 10 to 500 nm, with a homogeneous and unimodal distribution.

The more particularly preferred polymers according to the invention contain from 98 to 99.5% by weight of units of formula (1) and from 0.2 to 2% by weight of crosslinking units.

X⁺ represents a cation or a mixture of cations selected in particular from a proton, an alkali metal cation, a cation equivalent to that of an alkaline-earth metal or the ammonium ion. More particularly, 90 to 100 mol % of the cations are $NH_4^+$ cations and 0 to 10 mol % are protons ($H^+$).

The crosslinking monomers having at least two olefinic double bonds are selected, for example, from dipropylene glycol diallyl ether, polyglycol diallyl ethers, triethylene glycol divinyl ether, hydroquinone diallyl ether, tetraalkyloxethanoyl or other allyl or vinyl ethers polyfunctional alcohols, tetraethylene glycol diacrylate, triallylamine, trimethylolpropane diallyl ether, methylenebisacrylamide or divinylbenzene.

The crosslinking monomers having at least two olefinic double bonds are more particularly selected from those corresponding to the following formula (2):

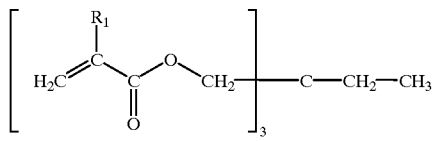
(2)

in which $R_1$ denotes a hydrogen atom or a $C_1$–$C_4$ alkyl and more particularly methyl (trimethylolpropane triacrylate).

The polymerization reaction of the polymers of the invention produces not only linear chains but also branched or crosslinked molecules of polymer. These molecules can be characterized in particular by their rheological behavior in water but more particularly by dynamic light scattering.

In the case of the characterization of the molecules by dynamic light scattering, the distribution of the hydrodynamic volume of the structures of the polymer is measured. Macromolecules dissolved in water are flexible and surrounded by a solvation envelope formed from water molecules. With charged polymers, such as those of the invention, the size of the molecules depends on the amount of salt in the water. In polar solvents, the uniform charge along the main chain of the polymer results in a significant expansion of the polymeric chain. The fact of increasing the amount of salt increases the amount of electrolyte in the solvent and screens the uniform charges of the polymer. In addition to the molecules transported in the salvation envelope, solvent molecules are fixed in the cavities of the polymer. In this case, the solvent molecules form part of the dissolved macromolecules and move at the same average speed. Thus, the hydrodynamic volume describes the linear dimension of the macromolecule and of these solvation molecules.

The hydrodynamic volume $V_h$ is determined by the following formula:

$$V_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d denoting the mass in grams of the solvent which is associated with 1 gram of undissolved macromolecule.

If the hydrodynamic particle is spherical, it is then easy to calculate the hydrodynamic radius from the hydrodynamic volume by the formula:

$$V_h = 4\pi R^3/3$$

with R denoting the hydrodynamic radius.

Cases where hydrodynamic particles are perfect spheres are extremely rare. The majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to distributions of molecular weight and thus with respect to distributions of hydrodynamic radius and volume. For polydispersed systems, it is necessary to calculate the distribution of the diffusion coefficients. From this distribution, the results relating to the radial distribution and to the distribution of the hydrodynamic volumes are deduced therefrom.

The hydrodynamic volumes of the polymers of the invention are in particular determined by dynamic light scattering from the Stokes-Einstein diffusion coefficients D of formula: $D = kT/6\pi\eta R$ where k is Boltzmann's constant, T is the absolute temperature in degrees Kelvin, $\eta$ is the viscosity of the solvent (water) and R is the hydrodynamic radius.

These diffusion coefficients D are measured according to the method of characterization of a mixture of polymers by laser scattering described in the following references:

(1) Pecora, R; Dynamic Light Scattering; Plenium Press, New York, 1976;

(2) Chu, B; Dynamic Light Scattering; Academic Press, New York, 1994;

(3) Schmitz, KS; Introduction to Dynamic Light Scattering; Academic Press, NewYork, 1990;

(4) Provincher S. W.; Comp. Phys., 27, 213, 1982;

(5) Provincher S. W.; Comp. Phys., 27, 229,1982;

(6) ALV Laservertriebgesellschaft mhH, Robert Bosch Str. 47, D-63225 Langen, Germany;

(7) ELS-Reinheimer Strasse 11, D-64846 Gross-Zimmern, Germany;

(8) Chi Wu et al., Macromolecules, 1995, 28, 4914–4919.

The particularly preferred polymers are those exhibiting a viscosity, measured with a Brookfield viscometer in a 2% solution in water at 25° C., of greater than or equal to 1000 cPs and more preferentially ranging from 5000 to 40,000 cPs and more particularly from 6500 to 35,000 cPs.

The crosslinked poly(2-acrylamido-2-methylpropanesulphonic acid)s of the invention can be obtained according to the preparation process comprising the following stages:

(a) the 2-acrylamido-2-methylpropanesulphonic acid monomer is dispersed or dissolved in the free form in a tert-butanol or water and tert-butanol solution;

(b) the solution or the dispersion of AMPS monomer obtained in (a) is neutralized with one or a number of inorganic or organic bases, preferably ammonia $NH_3$, in an amount which makes it possible to obtain a degree of neutralization of the sulphonic acid functional groups of the polymer ranging from 90 to 100%;

(c) the crosslinking monomer or monomers is/are added to the solution or dispersion obtained in (b);

(d) a conventional radical polymerization is carried out in the presence of free radical initiators at a temperature ranging from 10 to 150° C., the polymer precipitating in the solution or dispersion based on tert-butanol.

The virtually or completely neutralized crosslinked poly(2-acrylamido-2-methylpropanesulphonic acid)s are present in the cosmetic or dermatological compositions of the invention in concentrations preferentially ranging from 0.01 to 20% by weight with respect to the total weight of the composition and more preferentially from 0.1 to 10% by weight.

The proteins used according to the invention are those commonly used in cosmetics or in dermatology. They are of plant or animal origin and may or may not be hydrolysed.

Mention may be made, for example, among the plant proteins which can be used according to the invention, of:

soya proteins, such as the product in the form of an aqueous dispersion sold under the name ELESERYL by the company LSN;

wheat proteins, such as the hydrolysates sold under the name TRITISOL by the company Croda or those sold under the name VEGESERYL by the company LSN;

oat proteins, such as the product REDUCTINE sold by the company Silab;

pea proteins, such as the product ETIVAL sold by Coletica.

Mention may be made, for example, among the animal proteins which can be used according to the invention, of:

milk proteins, such as β-lactoglobulin, casein or whey;

serum proteins, such as horse serum;

placental proteins;

fibrous skin proteins, such as collagen or elastin.

The protein or proteins are present in concentrations preferably ranging from 0.001% to 30% by weight and more preferably from 0.01% to 10% by weight with respect to the total weight of the composition.

The compositions of the invention contain a cosmetically acceptable aqueous medium, that is to say a medium compatible with all keratinous substances, such as the skin, nails, mucous membranes and hair, or any other cutaneous region of the body.

The compositions preferably contain a cosmetically and/or dermatologically acceptable aqueous medium. They exhibit a pH which can preferably range from 1 to 13 and more preferentially from 2 to 12.

The cosmetically and/or dermatologically acceptable medium of the compositions according to the invention is more particularly composed of water and optionally of cosmetically and/or dermatologically acceptable organic solvents.

The organic solvents can represent from 5% to 98% of the total weight of the composition. They can be selected from the group composed of hydrophilic organic solvents, lipophilic organic solvents, amphiphilic solvents or their mixtures.

Mention may be made, among hydrophilic organic solvents, for example, of linear or branched lower monoalcohols having from 1 to 8 carbon atoms, such as ethanol, propanol, butanol, isopropanol or isobutanol; polyethylene glycols having from 6 to 80 ethylene oxide units; polyols, such as propylene glycol, isoprene glycol, butylene glycol, glycerol or sorbitol; mono- or dialkyl isosorbides, the alkyl groups of which have from 1 to 5 carbon atoms, such as dimethyl isosorbide; glycol ethers, such as diethylene glycol monomethyl or monoethyl ether and propylene glycol ethers, such as dipropylene glycol methyl ether.

Mention may be made, as amphiphilic organic solvents, of polyols, such as polypropylene glycol (PPG) derivatives, such as esters of polypropylene glycol and of fatty acid or ethers of PPG and of fatty alcohol, for example PPG-23 oleyl ether and PPG-36 oleate.

Mention may be made, as lipophilic organic solvents, for example, of fatty esters, such as diisopropyl adipate or dioctyl adipate, or alkyl benzoates.

In order for the cosmetic or dermatological compositions of the invention to be more pleasant to use (softer on application, more nourishing, more emollient), it is possible to add a fatty phase to the medium of these compositions.

The fatty phase preferably represents from 0% to 50% of the total weight of the composition. This fatty phase can contain one or a number of oils preferably selected from the group composed of:

water-soluble or liposoluble, organomodified or non-organomodified, linear, branched or cyclic, volatile or non-volatile silicones, mineral oils, such as liquid paraffin and liquid petrolatum, oils of animal origin, such as perhydrosqualene, oils of plant origin, such as sweet almond oil, avocado oil, castor oil, olive oil, jojoba oil, sesame oil, groundnut oil, macadamia oil, grape seed oil, rapeseed oil or coconut oil, synthetic oils, such as purcellin oil or isoparaffins, fluorinated and perfluorinated oils, esters of fatty acids, such as purcellin oil.

It can also contain, as fatty substance, one or a number of fatty alcohols, fatty acids (stearic acid) or waxes (paraffin wax, polyethylene waxes, carnauba wax or beeswax).

In a known way, all the compositions of the invention can contain adjuvants usual in the cosmetic and dermatological fields: other conventional hydrophilic or lipophilic gelling and/or thickening agents; hydrophilic or lipophilic active principles; preservatives; antioxidants; fragrances; emulsifiers; moisturizing agents; pigmenting agents; depigmenting agents; keratolytic agents; vitamins; emollients; sequestering agents; surfactants; polymers; basifying or acidifying agents; fillers; agents for combating free radicals; ceramides; sunscreen agents (in particular ultraviolet screening agents); insect repellents; slimming agents; coloring materials; bactericides; or antidandruff agents. The amounts of these various adjuvants are those conventionally used in the fields under consideration.

Of course, the person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in all the forms appropriate for a topical application, in particular in the form of solutions of the lotion or serum type, in the form of aqueous gels or in the form of emulsions obtained by dispersion of a fatty phase in an aqueous phase (O/W) or vice versa (W/O), with a liquid, semi-liquid or solid consistency, such as milks, more or less smooth creams, or pastes. These compositions are prepared according to the usual methods.

The compositions according to the invention can be used as rinse-out hair products or as leave-in hair products, in particular for washing, caring for, conditioning or form retention of the hairstyle or shaping keratinous fibers, such as the hair. They can be styling products, such as hair-setting lotions, blow-drying lotions or fixing and styling compositions. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray or a foam for fixing or treating the hair.

The compositions of the invention can also be shampoos or compositions of a rinse-out or leave-in nature to be applied before or after shampooing, dyeing, bleaching, perming or hair straightening.

The compositions of the invention can also be used as care and/or hygiene product, such as protection, treatment or care creams for the face, for the hands or for the body, protection or care body milks or lotions, gels or foams for caring for the skin and mucous membranes or for cleansing the skin. The compositions of the invention can also be used as anti-sun product. The compositions can be make-up products.

Another subject of the invention is a process for the non-therapeutic cosmetic treatment of the skin, scalp, hair, eyelashes, eyebrows, nails or mucous membranes, characterized in that a composition as defined above is applied on the keratinous substrate according to the usual technique for the use of this composition. For example: application of creams, gels, serums, lotions or milks on the skin, the scalp and/or the mucous membranes. The type of treatment depends on the protein or proteins present in the composition.

A further subject of the invention is the use of the above composition for preparing a lotion, a serum, a milk, a pomade or an ointment intended for the therapeutic treatment of keratinous substances, such as the skin, scalp, hair, eyelashes, eyebrows, nails or mucous membranes.

Another subject of the invention is the use of a crosslinked poly(2-acrylamido-2-methylpropanesulphonic acid) defined above as stabilizing agent in and for the preparation of a topical composition in the form of an oil-in-water or water-in-oil emulsion containing proteins of plant origin and/or proteins of animal origin, which may or may not be hydrolysed, and more particularly in and for the preparation of a topical composition in the form of an oil-in-water emulsion not containing surfactant.

The following examples illustrate the invention without having a limiting nature.

PREPARATION EXAMPLE A 2006.2 g of tert-butanol were introduced into a 5-liter round-bottomed flask equipped with a stirrer, a reflux condenser, a thermometer and a device for introducing nitrogen and ammonia, followed by 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 was obtained. 32.0 g of a 25% solution of trimethylolpropane triacrylate in tert-butanol were then introduced and the reaction mixture was heated to 60° C. while simultaneously being made inert by introducing nitrogen into the round-bottomed flask. Once this temperature had been reached, dilauroyl peroxide was added. The reaction began immediately, which was reflected by a rise in temperature and by precipitation of the polymerisate. 15 minutes after the beginning of the polymerization, a stream of nitrogen was introduced. 30 minutes after the addition of the initiator, the temperature of the reaction mixture reached a maximum of 65–70° C. 30 minutes after having reached this temperature, the reaction mixture was heated to reflux and was maintained under these conditions for 2 hours. During the reaction, the formation of a thick paste was observed. The reaction mixture was cooled to room temperature and the product obtained was filtered off. The recovered paste was then dried under vacuum at 60–70° C. for 24 hours. 391 g of crosslinked and neutralized poly(2-acrylamido-2-methylpropanesulphonic acid) were obtained with a viscosity, measured with a Brookfield viscometer, rotor 4, at a rotational speed of 100 revolutions/minute in a 2% solution in water at 25° C., ranging from 15,000 cPs to 35,000 cPs. The viscosity of the polymer can be selected and controlled according to conventional means, depending on the cosmetic application envisaged.

The hydrodynamic radius of the polymer obtained in an aqueous solution, determined by dynamic light scattering, was 440 nm.

PREPARATION EXAMPLE B 2006.2 g of tert-butanol were introduced into a 5-liter round-bottomed flask equipped with a stirrer, a reflux condenser, a thermometer and a device for introducing nitrogen and ammonia, followed by 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 was obtained. 19.2 g of a 25% solution of trimethylolpropane triacrylate in tert-butanol were then introduced and the reaction mixture was heated to 60° C. while simultaneously being made inert by introducing nitrogen into the round-bottomed flask. Once this temperature had been reached, dilauroyl peroxide was added. The reaction began immediately, which was reflected by a rise in temperature and by precipitation of the polymerisate. 15 minutes after the beginning of the polymerization, a stream of nitrogen was introduced. 30 minutes after the addition of the initiator, the temperature of the reaction mixture reached a maximum of 65–70° C. 30 minutes after having reached this temperature, the reaction mixture was heated to reflux and was maintained under these conditions for 2 hours. During the reaction, the formation of a thick paste was observed. The reaction mixture was cooled to room temperature and the product obtained was filtered off. The recovered paste was then dried under vacuum at 60–70° C.

for 24 hours. 391 g of crosslinked and neutralized poly(2-acrylamido-2-methylpropanesulphonic acid) were obtained with a viscosity, measured with a Brookfield viscometer, rotor 4, at a rotational speed of 100 revolutions/minute in a 2% solution in water at 25° C., of the order of 7000 cPs.

The hydrodynamic radius of the polymer obtained in an aqueous solution, determined by dynamic light scattering, was 160 nm.

EXAMPLE 1

Care gel for the skin

| | |
|---|---|
| Crosslinked poly(2-acrylamido-2-methyl-propanesulphonic acid) neutralized with ammonia, prepared according to the process of Preparation Example A, with a viscosity of the order of 16,000 cPs in a 2% solution in water at 25° C. | 2% by weight |
| Oat proteins, sold under the name of REDUCTINE by the company Silab | 7.0% by weight |
| Preservative q.s. | |
| Water q.s. for | 100% by weight |

PROCEDURE:

The gelling polymer was dispersed in water and the dispersion was homogenized with a propeller of Moritz type until a smooth gel was obtained and then the other ingredients were added in the order shown below while continuing to stir vigorously.

A smooth and glossy gel was obtained which was fresh on application and left the skin soft and matte.

EXAMPLE 2

Emulsifier-free serum for caring for the skin

| | |
|---|---|
| Crosslinked poly(2-acrylamido-2-methyl-propanesulphonic acid) neutralized with ammonia, prepared according to the process of Preparation Example A, with a viscosity of the order of 16,000 cPs in a 2% solution in water at 25° C. | 0.8% by weight |
| Soya proteins, sold under the name ELESERYL by the company LSN | 20% by weight |
| Glycerol | 5% by weight |
| Cyclomethicone | 6% by weight |
| Preservative q.s. | |
| Distilled water q.s. for | 100% by weight |

The preparation was carried out under the same conditions as Example 1.

A fluid and smooth product was obtained which has a very soft film-forming feel.

EXAMPLE 3

Care cream

| | |
|---|---|
| Phase 1 | |
| Polyethylene glycol stearate containing 20 mol of ethylene oxide, sold under the name MYRJ49 by ICI | 1% by weight |
| Glyceryl stearate and polyethylene glycol stearate containing 100 mol of ethylene oxide, sold under the name ARLACEL 165 by ICI | 1% by weight |

-continued

| | |
|---|---|
| Phase 1 | |
| Stearyl alcohol | 2% by weight |
| Stearic acid | 1% by weight |
| Hydrogenated isoparaffin | 20% by weight |
| Phase 2 | |
| Crosslinked poly(2-acrylamido-2-methyl propanesulphonic acid) neutralized with ammonia, prepared according to the process of Preparation Example A, with a viscosity of the order of 16,000 cPs in a 2% solution in water at 25° C. | 1.5% by weight |
| Glycerol | 3.0% by weight |
| Preservative q.s. | |
| Water q.s. for | 100% by weight |
| Phase 3 | |
| Wheat protein hydrolysate, sold under the name of TRITISOL XM by the company Croda | 15% by weight |

PROCEDURE:

Phases 1 and 2 were homogenized and heated separately to 70° C. The oily phase 1 was poured into the aqueous phase 2 with vigorous stirring (Moritz propeller). When the emulsion was fine, the mixture was cooled with paddle stirring to 35–40° C. Finally, the protein phase 3 was added.

A thick, rich and nourishing cream was obtained which leaves the skin supple and smooth.

We claim:

1. A cosmetic and/or dermatological composition comprising, in a cosmetically and/or dermatologically acceptable medium, at least one protein of plant origin or animal origin, wherein said at least one protein may or may not be hydrolysed, and at least one crosslinked poly(2-acrylamido-2-methylpropanesulphonic acid) neutralized to at least 90% comprises, distributed randomly:

a) from 90 to 99.9% by weight of units of following formula (1):

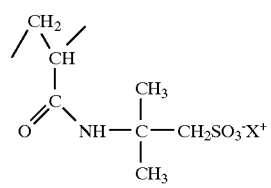

(1)

in which $X^+$ denotes a cation or a mixture of cations, it being possible for at most 10 mol % of the cations $X^+$ to be protons $H^+$; and b) from 0.01 to 10% by weight of crosslinking units resulting from at least one monomer having at least two olefinic double bonds, the proportions by weight being defined with respect to the total weight of the polymer.

2. A composition according to claim 1, wherein said at least one crosslinked poly(2-acrylamido-2-methylpropanesulphonic acid) contains a number of units of formula (1) in an amount which is sufficiently high to produce a hydrodynamic volume of the polymer in solution in water having a radius ranging from 10 to 500 nm, with a homogeneous and unimodal distribution.

3. A composition according to claim 1, wherein said at least one crosslinked poly(2-acrylamido-2- methylpropanesulphonic acid) contains from 98 to 99.5% by weight of units of formula (1) and from 0.2 to 2% by weight of crosslinking units.

4. A composition according to claim 1, wherein, in the formula (1), the cation $X^+$ is $NH_4^+$.

5. A composition according to claim 2, wherein said crosslinking monomer units correspond to the following formula (2):

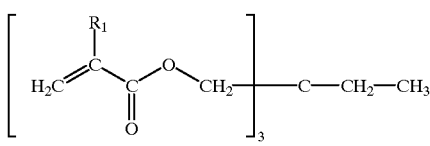

(2)

in which $R_1$ denotes a hydrogen atom or a $C_1$–$C_4$ alkyl.

6. A composition according to claim 1, wherein said poly(2-acrylamido-2-methylpropanesulphonic acid) is crosslinked with trimethylolpropane triacrylate.

7. A composition according to claim 1, wherein said at least one crosslinked poly(2-acrylamido-2-methylpropanesulphonic acid) exhibits a viscosity, measured with a Brookfield viscometer, rotor 4, at a rotational speed of 100 revolutions/minute in a 2% solution in water at 25° C., of greater than or equal to 1000 cPs.

8. A composition according to claim 7, wherein said at least one crosslinked poly(2-acrylamido-2-methylpropanesulphonic acid) exhibits a viscosity ranging from 5000 to 40,000 cPs.

9. A composition according to claim 8, wherein said at least one crosslinked poly(2-acrylamido-2-methylpropanesulphonic acid) exhibits a viscosity ranging from 6500 to 35,000 cPs.

10. A composition according to claim 1, wherein said at least one crosslinked poly(2-acrylamido-2-methylpropanesulphonic acid) is present in a concentration ranging from 0.01 to 20% by weight with respect to the total weight of the composition.

11. A composition according to claim 10, wherein said at least one crosslinked poly(2-acrylamido-2-methylpropanesulphonic acid) is present in a concentration ranging from 0.1 to 10% by weight with respect to the total weight of the composition.

12. A composition according to claim 1, wherein said plant proteins are soya proteins; wheat proteins; oat proteins; pea proteins, or the hydrolysates thereof.

13. A composition according to claim 1, wherein said animal proteins are milk proteins; serum proteins; placental proteins; or fibrous skin proteins.

14. A composition according to claim 1, wherein said at least one protein is present in a concentration ranging from 0.001% to 30% by weight with respect to the total weight of the composition.

15. A composition according to claim 14, wherein said at least one protein is present in a concentration ranging from 0.01% to 10% by weight with respect to the total weight of the composition.

16. A composition according to claim 1, wherein said cosmetically and/or dermatologically acceptable medium comprises water or water and at least one organic solvent wherein said at least one organic solvent is a hydrophilic organic solvent, a lipophilic organic solvent, an amphiphilic solvent or a mixture thereof.

17. A composition according to claim 16, wherein said at least one organic solvent is a mono- or polyfunctional alcohol, optionally oxyethylenated polyethylene glycol, propylene glycol ester, sorbitol, a derivative of sorbitol, dialkyl isosorbide, glycol ether, propylene glycol ether, or a fatty ester.

18. A composition according to claim 17, wherein said at least one organic solvent represents from 5% to 98% of the total weight of the composition.

19. A composition according to claim 1, additionally comprising at least one fatty phase.

20. A composition according to claim 19, wherein said fatty phase represents up to 50% of the total weight of the composition.

21. A composition according to claim 1, wherein said composition additionally contains at least one additive selected from the group consisting of conventional hydrophilic and lipophilic gelling and thickening agents; hydrophilic and lipophilic active principles; preservatives; antioxidants; fragrances; emulsifiers; moisturizing agents; pigmenting agents; depigmenting agents; keratolytic agents; vitamins; emollients; sequestering agents; surfactants; polymers; basifying and acidifying agents; fillers; agents for combating free radicals; ceramides; sunscreen agents; insect repellents; slimming agents; coloring materials; bactericides; and antidandruff agents.

22. A composition according to claim 21, wherein said sunscreen agents are ultraviolet screening agents.

23. A rinse-out or leave-in hair product for washing, caring for, conditioning or retaining the form of a hairstyle or shaping the hair, said product comprising a cosmetic and/or dermatological composition according to claim 1.

24. A care and/or hygiene product, said product comprising a cosmetic and/or dermatological composition according to claim 1.

25. A make-up product, said product comprising a cosmetic and/or dermatological composition according to claim 1.

26. An anti-sun product, said product comprising a cosmetic and/or dermatological composition according to claim 1.

27. A process for the non-therapeutic and cosmetic treatment of a substrate selected from the skin, scalp, hair, eyelashes, eyebrows, nails and mucous membranes, said process comprising applying on said substrate a cosmetic and/or dermatological composition according to claim 1.

28. A cosmetic and/or dermatological composition according to claim 1, wherein said composition is in the form of a lotion, a serum, a milk, a pomade or an ointment intended for the therapeutic treatment of the skin, scalp, hair, eyelashes, eyebrows, nails or mucous membranes.

29. A process for preparing a topical composition in the form of an oil-in-water or water-in-oil emulsion containing at least one protein of plant origin or animal origin, wherein said at least one protein may or may not be hydrolysed, said process comprising including in said composition at least one crosslinked poly(2-acrylamido-2-methylpropanesulphonic acid) neutralized to at-least 90% as a stabilizing agent comprises, distributed randomly:

a) from 90 to 99.9% by weight of units of following formula (1):

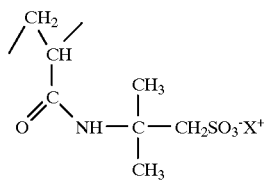

(1)

in which X⁺ denotes a cation or a mixture of cations, it being possible for at most 10 mol % of the cations X⁺ to be protons H⁺; and b) from 0.01 to 10% by weight of crosslinking units resulting from at least one monomer having at least two olefinic double bonds, the proportions by weight being defined with respect to the total weight of the polymer.

30. A process for preparing a topical composition in the form of a surfactant-free oil-in-water emulsion containing a fatty phase, an aqueous phase, and at least one protein of plant origin or animal origin, wherein said at least one protein may or may not be hydrolysed, said process comprising including in said composition at least one crosslinked poly(2-acrylamido-2-methyl-propanesulphonic acid) neutralized to at least 90% as a stabilizing agent comprises, distributed randomly:

a) from 90 to 99.9% by weight of units of following formula (1):

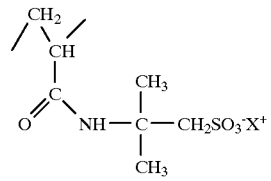

(1)

in which X⁺ denotes a cation or a mixture of cations, it being possible for at most 10 mol % of the cations X⁺ to be protons H⁺; and b) from 0.01 to 10% by weight of crosslinking units resulting from at least one monomer having at least two olefinic double bonds, the proportions by weight being defined with respect to the total weight of the polymer.

* * * * *